United States Patent [19]

Alliger et al.

[11] Patent Number: 5,397,293
[45] Date of Patent: Mar. 14, 1995

[54] ULTRASONIC DEVICE WITH SHEATH AND TRANSVERSE MOTION DAMPING

[75] Inventors: Howard M. Alliger, Melville; Ronald R. Manna, Valley Stream; Vaclav Padany, New Fairfield, all of N.Y.

[73] Assignee: Misonix, Inc., Farmingdale, N.Y.

[21] Appl. No.: 981,241

[22] Filed: Nov. 25, 1992

[51] Int. Cl.⁶ .......................................... A61B 17/22
[52] U.S. Cl. ........................................ 601/2; 606/128
[58] Field of Search .................. 128/24 AA; 606/128, 606/169; 604/22; 601/2

[56] References Cited

U.S. PATENT DOCUMENTS

| | | | |
|---|---|---|---|
| 4,431,006 | 2/1984 | Trimmer et al. | 128/24 AA |
| 4,870,953 | 10/1989 | DonMicheal et al. | 128/24 AA |
| 4,920,954 | 5/1990 | Alliger et al. | |
| 5,026,387 | 6/1991 | Thomas | 128/24 AA |
| 5,029,588 | 7/1991 | Yock et al. | |
| 5,058,570 | 10/1991 | Idemoto et al. | 128/24 AA |
| 5,123,903 | 6/1992 | Quaid et al. | 128/24 AA |
| 5,160,336 | 11/1992 | Favre | 606/128 |
| 5,167,619 | 12/1992 | Wuchinich | 128/24 AA |
| 5,242,385 | 9/1993 | Strukel | 128/24 AA |
| 5,267,954 | 12/1993 | Nita | |
| 5,269,297 | 12/1993 | Weng et al. | 601/2 |

FOREIGN PATENT DOCUMENTS

WO9211815  7/1992  WIPO.

*Primary Examiner*—Lee S. Cohen
*Assistant Examiner*—Brian L. Casler
*Attorney, Agent, or Firm*—R. Neil Sudol; Henry D. Coleman

[57] ABSTRACT

An ultrasonic angioplasty device for use in removing unwanted material from the vascular system of a patient comprises a wire having a proximal end, a sheath or catheter surrounding the wire, and a wave generator operatively connected to the wire at the proximal end for generating an ultrasonic waveform and transmitting the waveform axially along the wire. The ultrasonic device further comprises one or more projections extending radially inwardly from the sheath or catheter towards the wire at a plurality of predetermined axial motion nodes along the wire for minimizing transverse motion of the wire while permitting axial motion of the wire during transmission of the waveform along the wire.

23 Claims, 3 Drawing Sheets

ULTRASONIC DEVICE WITH SHEATH AND TRANSVERSE MOTION DAMPING

FIELD OF THE INVENTION

This invention relates to an ultrasonic device including an ultrasonic waveguide in the form of a wire extending through an elongate sheath or catheter. More particularly, this invention relates to such a device provided with means for damping traverse motion of the wire during ultrasonic wave transmission. This invention also relates to an associated method for use in transmitting an ultrasonic axial standing wave down a waveguide wire. This invention is directed particularly to an ultrasonic angioplasty device and an associated method for use in removing unwanted material such as plaque and blood clots from the vascular system of a patient.

BACKGROUND OF THE INVENTION

Removal of arterial plaque and blood clots by ultrasound is a new atherectomy method, taking its place as an important blood vessel cleaning device. Other devices now used for this purpose work by a process of cutting, scraping or slicing the obstruction within the artery or blood vessel. All atherectomy devices are two to five feet long, and less than 3 mm in diameter, small enough to be threaded through the arterial system to the coronary arteries, or small arteries of the leg.

Unlike cutting or scraping devices which have a rotating wire transmitting motion to a spinning tip, an ultrasonic system uses a thin wire to transmit sound waves to the distal working end. The wire, when tuned to the generator frequency, maintains a standing sound wave down its length. This wave is a compressional, axial, motion, where the molecules are stressed by compression and tension at the nodes or point of no movement, and the molecules are moving back and forth at great speed through the points known as anti-nodes.

When the distal tip of the wire vibrates in liquid such as blood, if the amplitude of movement is large enough, it causes cavitation, the making and breaking of bubbles. These bubbles are microscopic and extremely numerous. They collapse with great force producing a shearing and tearing action on any material in the bubble field. The large forces involved, although on a micron level, can, for example, in a mechanical system, cause boat propellers and pump cylinders to erode.

In order to negotiate the sinuous turns of the blood vessels, especially the curves entering the coronary arteries, the wire must be made thin. This small size provides the necessary flexibility so that the wire can be threaded easily to the occlusion. As the wire diameter is reduced, however, below approximately 0.030" (¾ mm), a problem arises. There appears a degree of freedom for lateral or transverse motion in the wire which is detrimental to the operation of the system. This tendency toward perpendicular vibration reduces the axial, or forward and backward, motion of the wire tip and also produces fatigue in the wire. This fatigue weakens the wire and tends to break it. It can be easily understood that if a thin wire touches an obstruction, such as arterial plaque, the wire would be especially vulnerable to whipping motion since instead of going forward into the occlusion, the wire more easily moves sideways. The reduction of axial motion results in lowered cavitation at the wire tip and reduces plaque or clot removal. For reasons of both danger to the wire integrity, as well as the reduction of cavitation intensity, it is vital to suppress the unwanted transverse motion.

In prior pending U.S. patent application Ser. No. 07/632,679, transverse motion is suppressed by a close fitting catheter or sheath surrounding the wire, and also a liquid flowing between wire and sheath. However, as the wire must be made even thinner and more flexible, the unwanted vibration problem again arises since the wire more easily tends to shiver.

OBJECTS OF THE INVENTION

An object of the present invention is to provide an ultrasonic cavitation device of the above-described type having a new and different feature for reducing or eliminating this small transverse motion or shivering action.

Another object of the present invention is to provide such an ultrasonic cavitation device which has an enhanced efficacy in reducing this transverse motion or shivering action in devices with thinner and more flexible waveguide wires.

A further object of the present invention is to provide a method for damping transverse motion along an ultrasonic waveguide without substantially limiting axial motion of the waveguide.

A more particular object of the present invention is to provide such an ultrasonic cavitation device which has a tapered wire waveguide.

Yet another particular object of the present invention is to provide such an ultrasonic cavitation device which has a sheath with internal projections for holding or touching the wire waveguide to damp lateral motion thereof.

These and other objects of the present invention will be apparent from the drawings and detailed descriptions herein.

SUMMARY OF THE INVENTION

An ultrasonic angioplastic surgical device comprises, in accordance with one embodiment of the present invention, a wire having a proximal end, a sheath or catheter surrounding the wire, and a wave generator operatively connected to the wire at the proximal end for generating an ultrasonic waveform and transmitting the waveform axially along the wire. The ultrasonic device further comprises a plurality of projections extending radially inwardly from the sheath or catheter towards the wire at one or more predetermined axial motion nodes along the wire for minimizing transverse motion of the wire while permitting axial motion of the wire during transmission of the waveform along the wire. The projections at any one node are circumferentially spaced from one another, thereby permitting a fluid to flow between the wire and the sheath and past the axial motion node.

Holding or touching of the vibrating wire at one or more node points established by the axial standing wave does not interfere with the desired wire movement longitudinally, since these nodes are points of no movement in the (useful) axial wave. However, such holding or touching in accordance with the present invention does minimize or damp undesirable transverse movement of the wire waveguide.

According to further features of this embodiment the present invention, the projections include one or more threads extending in a substantially radial plane at an axial motion nodes, each of the threads having opposite ends connected to the sheath. The threads may be parallel to one another or perpendicular to one another. In a specific realization of this embodiment of the invention, a first pair of parallel threads extend substantially orthogonally to a second pair of parallel threads, the wire passing between the members of each pair.

According to another feature of the first embodiment of the present invention, the projections include at a given node a plurality of hair-like protrusions extending inwardly from the sheath, each of the protrusions having a free end in engagement with the wire at the given node. The hair-like protrusions are preferably an integral part of the sheath.

According to an additional feature of the first embodiment of the present invention, a plurality of hair-like protrusions extend inwardly from the sheath and have free ends in engagement with the wire along a predetermined length of the wire including the given node and extending beyond the given node into a region of axial motion of the wire. The protrusions may be disposed in a cylindrical array.

According to yet another feature of the first embodiment the present invention, the projections include a dimple formed in the sheath at one of the nodes. The dimple may be one of a plurality of dimples or indentations in a circular array.

An ultrasonic angioplastic surgical device comprises, in accordance with another embodiment of the present invention, a wire having a proximal end, a sheath or catheter surrounding the wire, and a wave generator operatively connected to the wire at the proximal end for generating an ultrasonic waveform and transmitting the waveform axially along the wire. A solid transverse motion damping element or series of elements is disposed within the sheath along an area of axial motion of the wire for minimizing transverse motion of the wire while permitting axial motion of the wire during transmission of the waveform along the wire.

Pursuant to another feature of the present invention, the motion damping element or elements are connected to the sheath or catheter. Specifically, such transverse motion damping elements may include a plurality of hair-like protrusions extending inwardly from the sheath and in engagement with the wire along the area of axial motion. Such protrusions may be disposed in a cylindrical array.

Alternatively or additionally, the motion damping element includes an elongate axially oriented ridge having a knife-like edge juxtaposed to the wire. The knife-like edge of the ridge causes as little axial friction as possible.

In an alternative specific embodiment of the present invention, the damping element takes the form of an auxiliary wire which floats in the catheter or sheath alongside the ultrasonic waveguide.

An ultrasonic angioplasty device comprises, in accordance with yet another embodiment of the present invention, a wire having a proximal end, a sheath or catheter surrounding the wire, and wave generator means operatively connected to the wire at the proximal end for generating an ultrasonic waveform and transmitting the waveform axially along the wire, the wire being tapered along a predetermined substantial portion of its length for minimizing transverse motion of the wire while permitting axial motion of the wire during transmission of the waveform along the wire.

A method for removing unwanted material from the vascular system of a patient comprises, in accordance with the present invention, the steps of (a) providing a wire surrounded by a sheath or catheter, (b) threading the wire through labyrinthine vascular passages until a distal end of the wire is disposed at the location of the unwanted material, (c) generating an ultrasonic waveform at a proximal end of the wire, (d) transmitting the waveform axially along the wire from the proximal end, and (e) damping transverse motion of the wire while permitting axial motion of the wire during transmission of the waveform along the wire, the step of damping including the step of touching or holding the wire at one or more predetermined axial motion nodes along the wire.

Pursuant to another feature of the present invention, the step of touching or holding is implemented only at the predetermined axial motion node or nodes.

A method for removing unwanted material from the vascular system of a patient comprises, in accordance with the present invention, the steps of (i) providing a wire surrounded by a sheath or catheter, (ii) threading the wire through labyrinthine passages until a distal end of the wire is disposed at the location of the unwanted material, (iii) generating an ultrasonic waveform at a proximal end of the wire, (iv) transmitting the waveform axially along the wire from the proximal end, and (v) damping transverse motion of the wire while permitting axial motion of the wire during transmission of the waveform along the wire, the step of damping including the step of touching or holding the wire along a length thereof which moves axially under action of the waveform.

All of the particular methods in accordance with the present invention prevent transverse motion of the ultrasonic guide wire and allow liquid, if necessary, to flow down the sheath or catheter at the same time. Each reduction method alone, or in combination with the others, then minimizes the danger of the wire breaking and maximizes cavitation intensity at the wire tip.

DETAILED DESCRIPTION

Figure 1:
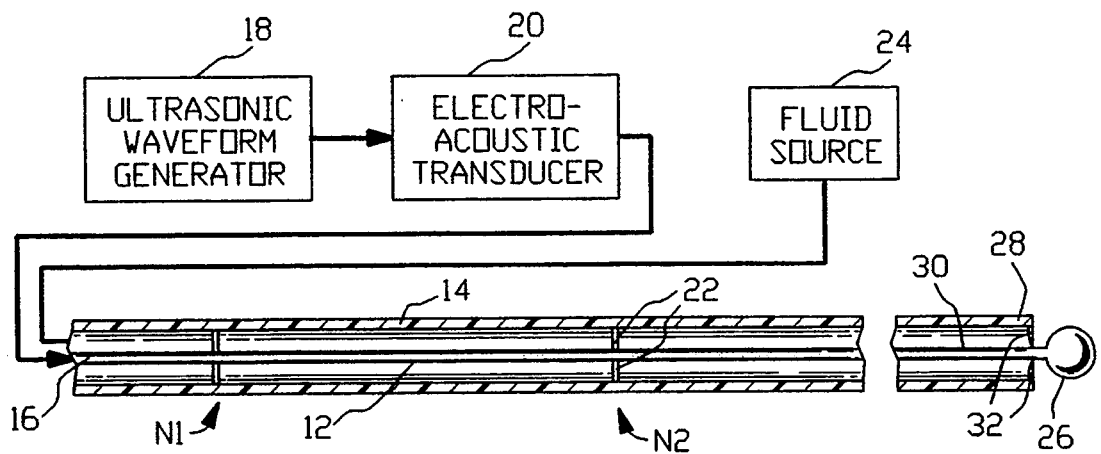
FIG. 1 is partially a block diagram and partially a schematic partial longitudinal cross-sectional view, on an enlarged scale, of an ultrasonic device in accordance with the present invention.

As illustrated in FIG. 1, an ultrasonic device particularly useful in removing blood clots another vascular blockages by a cavitation process comprises an ultrasonic waveguide in the form of a wire 12. A sheath or catheter 14 surrounds wire 12. Wire 12 has a proximal end 16 to which an ultrasonic waveform generator 18 is operatively connected via an elctro-acoustic transducer 20, as described in U.S. Pat. No. 4,920,954, the disclosure of which is hereby incorporated by reference.

Generator 18 produces an electrical waveform of an ultrasonic frequency which is converted into a pressure wave by transducer 20. The ultrasonic pressure wave is transmitted as an axial standing wave along wire 12. The ultrasonic device of FIG. 1 further comprises a plurality of projections 22 extending radially inwardly from sheath or catheter 14 towards wire 12 at a plurality of predetermined axial motion nodes N1, N2, etc. along wire 12. Projections 22 serve to minimize or damp transverse motion of wire 12 while permitting axial motion thereof during transmission of the axial ultrasonic pressure waveform along the wire. Projections 22 are angularly or circumferentially spaced from one another to permit the flow of fluid from source 24 through sheath 14 and along ultrasonic waveguide wire 12.

The holding or touching of vibrating wire 12 at node points N1, N2, ... established by the axial standing wave does not interfere with desired longitudinal wire movement but does serve to damp undesirable transverse movement of waveguide wire 12. It is to be noted that node N1, N2, ... need not be consecutive nodal points.

As illustrated schematically in FIG. 1 and described in detail in U.S. Pat. No. 4,920,954, a fluid source 24 is operatively connected to and in communication with sheath or catheter 14 for delivering a desired fluid (e.g., X-ray opaque liquid, an anticlotting agent such as heparin, etc.) to the distal end of the sheath. A ball 26 is fixed to the distal end of wire 12 for producing the cavitation effect characteristic of the ultrasonic device.

As further illustrated in FIG. 1, sheath or catheter 14 has a distal end 28 proximate to a distal end 30 of wire 12, the sheath being narrowed or pinched at its distal end, at 32, so that sheath 14 is in close juxtaposition to wire 12 around the circumference thereof, proximate to ball 28. Narrowing 32 may be implemented by tapering the distal end 28 of sheath 14 or by forming inwardly extending projections on the sheath. The projections 32 may be angularly or circumferentially spaced from one another to allow fluid to flow from the distal end 28 of sheath 14. The projections 32 may be sufficiently dense or numerous to ensure that fluid pressure is maintained inside sheath 14 at a predetermined level. In some applications, a high intraluminal pressure may be desired. In such cases, the distal end narrowing 32 of sheath 14 may be effectuated by a single annular projection or flange.

Distal end 30 of wire 12 is a particularly critical point. Ball 26 protects arterial walls of a patient from injury during use of the ultrasonic device of FIG. 1 in an angioplastic surgical operation and also increases the area of cavitation. When wire 12 is energized, ball 26 tends to vibrate transversely and thus place particular stress on the wire/ball attachment point due to the ball's mass. It is critical to prevent this transverse motion. Narrowing 32 at distal end 28 of sheath 14 touches or almost touches wire 12 around the circumference thereof, near ball 26, thereby preventing most of the transverse motion of the ball. The point of plane of contact of narrowing 32 with wire 12 is not at a node point, but because the sheath is touching on a narrow single circle, there is minimal loss and friction due to axial rubbing. The extra power necessary to maintain amplitude is quite small.

In FIGS. 2–10, a waveguide wire is designated by the same reference numeral 12 inasmuch as that element of the ultrasonic device is the same in the respective particular embodiments of the device. The sheaths or catheters of FIGS. 2–10 have different reference numerals inasmuch as their structure differs one from the other.

Figure 2:
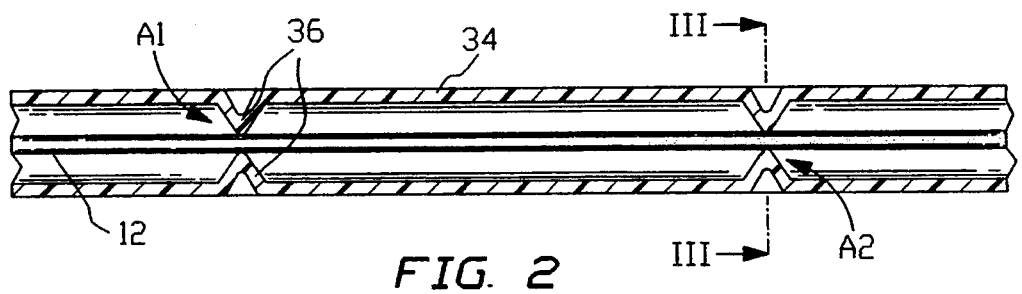
FIG. 2 is a schematic partial longitudinal cross-sectional view, on a larger scale, of a specific embodiment of an ultrasonic waveguide and sheath shown in FIG. 1.
Figure 3:
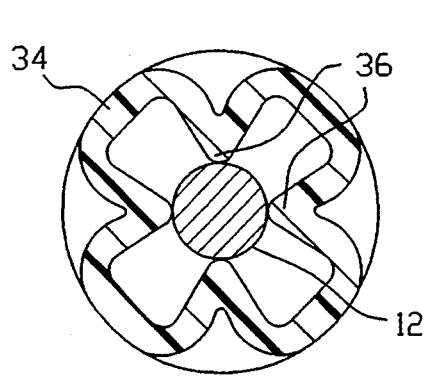
FIG. 3 is a transverse cross-sectional view taken along line III—III in FIG. 2.

As depicted in FIGS. 2 and 3, a waveguide sheath or catheter 34 in a particular embodiment of the cavitation device of FIG. 1 is provided with projections in the form of indentations or dimples 36 for damping transverse motion of wire 12. Indentations 36 are disposed in circular arrays A1, A2, etc., in planes located at nodes of the ultrasonic axial standing wave propagated along wire 12 during use of the cavitation device of FIG. 1.

Figure 4:
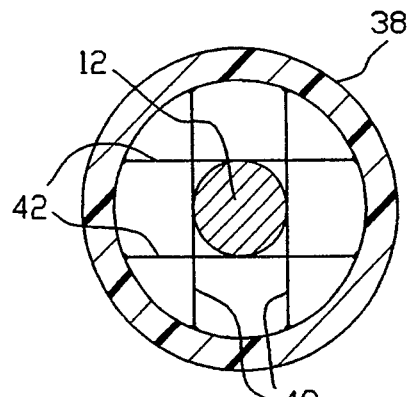
FIG. 4 is a transverse cross-sectional view of another specific embodiment of an ultrasonic waveguide and sheath in accordance with the present invention.

In another specific embodiment of the transverse damping feature, shown in FIG. 4, an ultrasonic waveguide sheath or catheter 38 is provided at each of a plurality of axial-motion nodes with damping projections in the form of a first pair of substantially parallel threads 40 and a relatively orthogonal second pair of substantially parallel threads 42 extending in a substantially radial plane at one of the nodes (the plane of the paper). Each thread 40 and 42 has opposite ends connected to sheath 38. Wire 12 passes between the threads 40 and 42 of each thread pair.

It is to be noted that a significant damping effect might also be achieved with fewer threads, for example, only one thread of each pair of threads 40 and 42. It is to be additionally noted that the angle between threads 40 and 42 need not be 90°, as illustrated in FIG. 4, but may be an acute angle. Additionally, threads 40 and 42 of each pair need not be parallel to one another.

In a non-illustrated modification of the embodiment of FIG. 4, three threads each oriented at an acute angle (e.g., 60°) to the other two threads are disposed in a nodal plane for damping transverse motion of wire 12.

Figure 5:
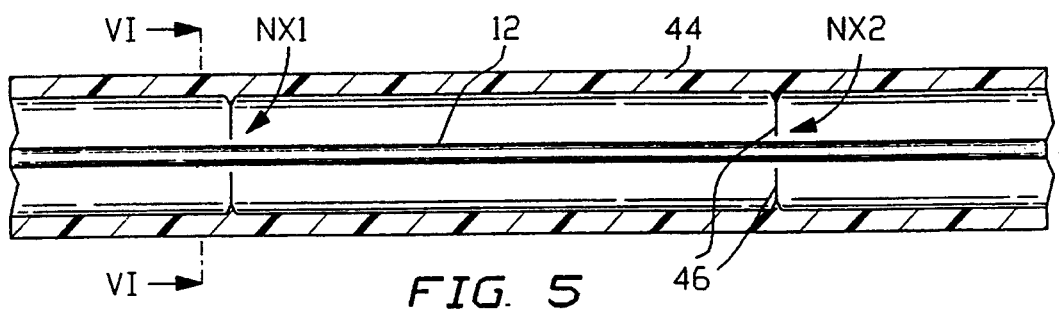
FIG. 5 is a schematic partial longitudinal cross-sectional view, on an even larger scale, of another specific embodiment of the ultrasonic waveguide and sheath shown in FIG. 1.
Figure 6:
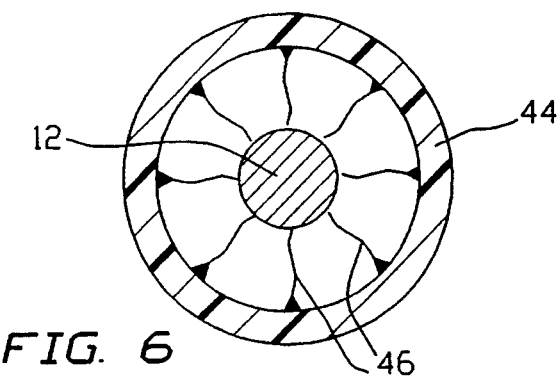
FIG. 6 is a transverse cross-sectional view taken along line VI—VI in FIG. 5.

As shown in FIGS. 5 and 6, an ultrasonic waveguide sheath or catheter 44 is provided at each of a plurality of axial-motion nodes NX1, NX2, ... with damping projections in the form of hair-like protrusions 46 extending radially inwardly from sheath 44. Protrusions 46 have free ends 48 in close juxtaposition to or in engagement with wire 12 at the respective node and are preferably an integral part of sheath 44.

According to an additional feature of the first embodiment of the present invention, a plurality of hair-like protrusions extend radially inwardly from the sheath and have free ends closely juxtaposed to or in engagement with wire 12a predetermined length of the wire including the given node and extending beyond the given node into a region of axial motion of the wire. The protrusions may be disposed in a cylindrical array.

Figure 7:
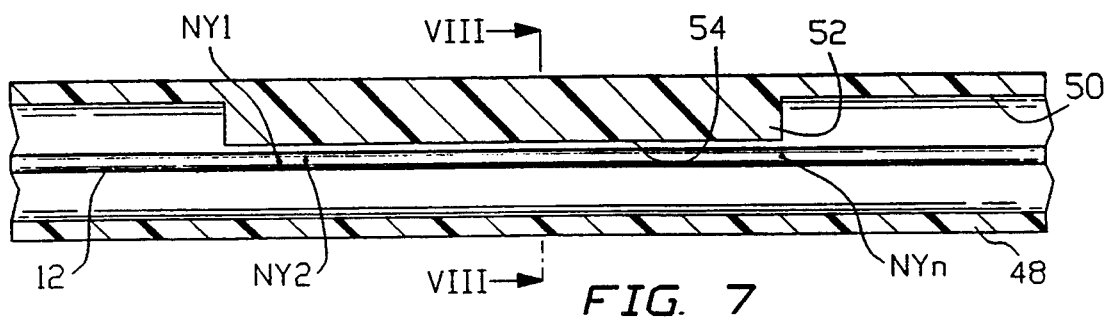
FIG. 7 a schematic partial longitudinal cross-sectional view, again on an enlarged scale, of a further ultrasonic waveguide and sheath of an ultrasonic device in accordance with the present invention.
Figure 8:
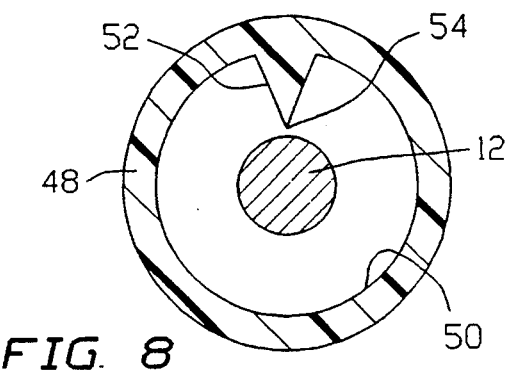
FIG. 8 is a transverse cross-sectional view taken along line VIII—VIII in FIG. 7.

As depicted in FIGS. 7 and 8, a sheath or catheter 48 of an ultrasonic device as illustrated in FIG. 1 is provided along a lumen surface 50 with a transverse motion damping element in the form of an elongate, longitudinally or axially extending ridge 52 having a substantially triangular cross-section. Ridge 52 has a sharp or knifelike, longitudinally or axially extending edge 54 disposed in close juxtaposition or engagement with wire 12 along a substantial portion of the length of the wire which includes a plurality of axial-motion nodal points NY1, NY2, ... NYn.

Knife-like edge 54 of ridge 52 causes as little axial friction as possible. Although ridge 52 could be touching at all points along the length of edge 54, node and anti-node alike, the transverse damping action would be far greater than the axial damping action. It is necessary, of course, to supply more power to compensate for axial frictional losses and to maintain tip amplitude.

It is to be noted that ridge 52 is disposed within the sheath along an area of axial motion of wire 12 for minimizing transverse motion of the wire while permitting axial motion of the wire during transmission of an ultrasonic standing waveform along the wire.

Figure 9:
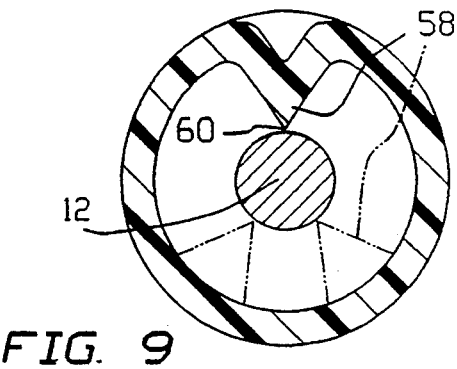
FIG. 9 is a transverse cross-sectional view similar to FIG. 8, showing an alternative design in accordance with the present invention.

FIG. 9 illustrates a variation of the embodiment of FIGS. 7 and 8. A catheter or sheath 56 for ultrasonic waveguide wire 12 is provided in a predetermined region with one or more elongate, longitudinally extending indentations 58 each having a sharp or knife-like inner edge 60 in close juxtaposition or engagement with wire 12.

Figure 10:
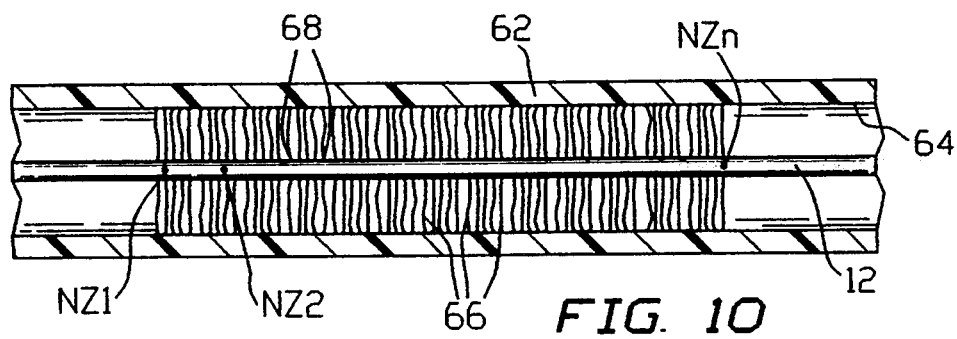
FIG. 10 is a schematic partial longitudinal cross-sectional view, also on an enlarged scale, of yet another ultrasonic waveguide and sheath of an ultrasonic device in accordance with the present invention.

As shown in FIG. 10, a catheter or sheath 62 for ultrasonic waveguide wire 12 is formed along an inner surface 64 with a multiplicity of hair-like protrusions 66 extending inwardly from inner surface 64 for damping transverse motion of wire 12 during an ultrasonic cavitation procedure. Protrusions 66 have free ends 68 closely juxotaposed to or in engagement with wire 12 along an area including a plurality of axial motion nodes NZ1, NZ2, ... NZn. Protrusions 66 may be disposed in a cylindrical array (see FIG. 6).

"Hairy" sheath 62 may be constructed by first raising hairs or protrusions 66 on a flat sheet of semi molten plastic. The flat sheet can be cut to size and rolled into a tube, with the long edge then being attached by plastic welding or glueing. Hairs 66 provide little restriction to the axial wire motion since the hairs can move back and forth easily, but are sturdy in the compressional mode. In this way, shivering of the wire would be damped with little resistance to axial movement.

Figure 11:
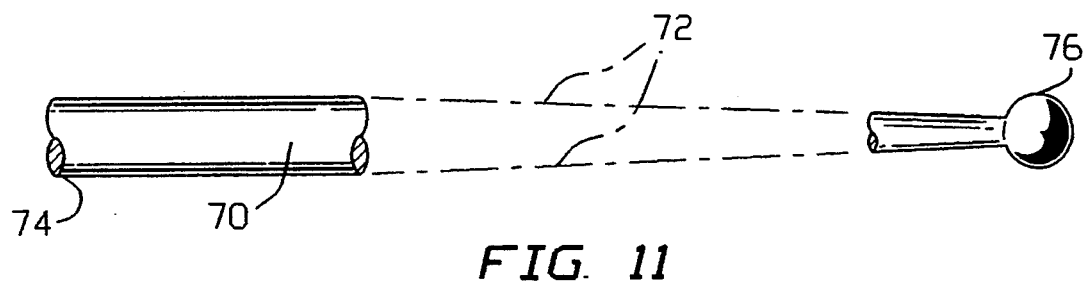
FIG. 11 is a schematic partial side elevational view of a waveguide wire in accordance with the present invention.

As illustrated in FIG. 11, another method for reducing the transverse motion of a waveguide wire 70 in an ultrasonic cavitation device as described in U.S. Pat. No. 4,920,954 is to provide wire 70 with a taper, as indicated by dot-dash lines 72. Wire 70 is tapered along a predetermined substantial portion of its length for minimizing transverse motion of the wire while permitting axial motion of the wire during transmission of the waveform along the wire. The taper illustrated in FIG. 11 is most advantageous when it extends down the entire length of wire 70, starting at the wire's proximal connection point 74 and ending at a ball 76 at the distal tip. A typical taper in such a design is from 0.035" to 0.018" diameter (or roughly 1 mm to ½ mm). Tapering of the wire waveguide has the additional advantage of greater strength and sound carrying capacity near the proximal connection point, while providing great flexibility near the distal tip. Tapers could also start at other points, for example, half way down the length of the wave guide wire, and extend to the distal tip. As it turns out, the transverse frequency of the wire will vary as the wire diameter changes, so that the many different natural transverse frequencies now along the length tend to interfere, and cancel, rather than reinforce one another.

It is to be noted that wire 70 may be used with a sheath (not illustrated) having an inner diameter which decreases along a length of the sheath coextensive with taper 72. In this case, the inner diameter of the sheath remains small enough to inhibit or damp significant transverse motion of the wire 70 and is large enough to not impede axial motion. The inner diameter of the sheath is, for example, between 0.005" and 0.012" larger than the outer diameter of the wire. The presence in the sheath of a viscous fluid such as contrast medium, plasma, sodium hyaluronate, or dextran further decreases lateral motion of the wire while only slightly decreasing the drag on the wire's axial motion. Pressure may be applied (e.g., via a syringe or pump, not illustrated) on the liquid in the sheath in order to enhance the damping effect on the transverse motion. Such pressurization of liquid in a catheter or sheath may be implemented to enhance transverse motion damping in other ultrasonic waveguide assemblies described above with reference to FIGS. 1-10 and below with reference to FIG. 12.

Figure 12:
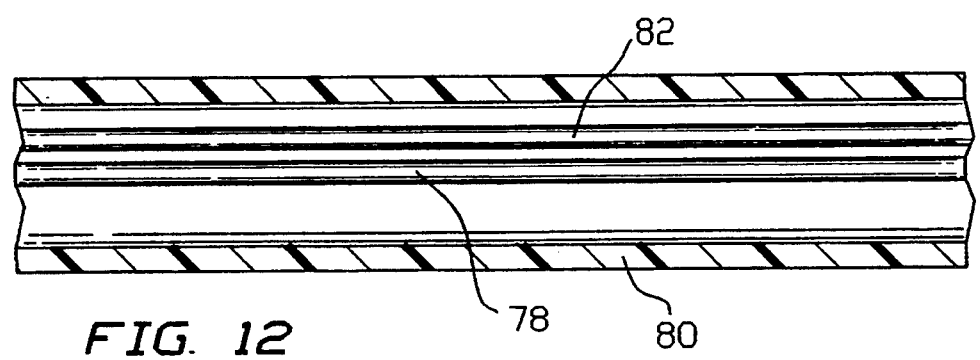
FIG. 12 is a schematic partial longitudinal cross-sectional view, also on an enlarged scale, of an additional ultrasonic waveguide and sheath of an ultrasonic device in accordance with the present invention.

As depicted in FIG. 12 another ultrasonic cavitation device with transverse motion damping comprises an ultrasonic waveguide wire 78 connected at a proximal end to a wave generator (not shown) which produces an ultrasonic waveform and transmits the waveform axially along the wire. A sheath 80 surrounds wire 78, while a solid transverse motion damping element in the form of a thread or auxiliary wire 82 is disposed within the sheath along an area of axial motion of wire 78 so as to minimize transverse motion of the wire while permitting axial motion of the wire during transmission of the waveform along the wire. Damping wire 82 is separate from sheath 80 and floats therein during use of the ultrasonic cavitation device.

An advantage of damping wire 82 is that, in not being attached to sheath 80, the auxiliary wire does not inhibit bending of the ultrasonic device during insertion thereof through vascular passageways. Specifically, damping wire 82 could be made of titanium and have a diameter of approximately 0.005 inch (⅛ mm). Damping wire 82 touches waveguide wire 78 randomly along the length of wire 82. Wire 82 permits substantially unimpeded axial motion of wire 78 but damp transverse motion thereof. Wire 82 is preferably approximately as long as sheath 80. However, shorter lengths can be satisfactory.

In using any specific embodiments of the ultrasonic cavitation device disclosed herein, wire 12 surrounded by the respective sheath or catheter is threaded through labyrinthine passages (such as patient's blood vessels) until a distal end of the wire is disposed at the location of unwanted material (e.g., plaque, a blood clot, etc.). An ultrasonic waveform is then generated by a crystal and imparted to a proximal end of wire 12 and transmitted as a standing wave axially along the wire. Transverse motion of wire 12 is damped while permitting axial motion of the wire during transmission of the waveform along the wire. As described hereinabove with reference to FIGS. 1-10, the damping may be accomplished by touching or holding wire 12 at a plurality of predetermined axial motion nodes along the wire. Specifically, the touching or holding of the wire may be implemented only at the plurality of predetermined axial motion nodes (FIGS. 1-6). Alternatively, the touching or holding of the wire 12 may be implemented along a length of the wire which moves axially under action of the waveform.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. An ultrasonic angioplasty device for use with an ultrasonic waveform generator, comprising:
    a wire having a proximal end operatively connectable to said waveform generator;
    a sheath surrounding said wire; and
    transverse motion damping means disposed within said sheath for minimizing transverse motion of the wire while permitting axial motion of said wire during transmission of an ultrasonic waveform along said wire, said motion damping means including a thread extending in a substantially radial plane inside said sheath, said thread having opposite ends connected to said sheath.

2. The device defined in claim 1 wherein said thread is one of a plurality of threads disposed in said plane, each of said threads having opposite ends connected to said sheath.

3. The device defined in claim 2 wherein said threads are parallel to one another.

4. The device defined in claim 2 wherein said threads are perpendicular to one another.

5. The device defined in claim 1 wherein said thread is disposed at a predetermined axial motion node along said wire.

6. An ultrasonic angioplasty device for use with an ultrasonic waveform generator, comprising:
    a wire having a proximal end operatively connectable to said waveform generator;
    a sheath surrounding said wire; and
    a solid transverse-motion-damping element connected to said sheath and disposed within said sheath along an area of axial motion of said wire spaced from each axial motion node of said wire so as to minimize transverse motion of the wire while permitting axial motion of said wire during transmission of an ultrasonic waveform along said wire.

7. The device defined in claim 6 wherein said damping element includes a portion of a wall of said sheath and a plurality of hair-like protrusions connected to said wall and extending inwardly from said sheath and in engagement with said wire along a predetermined length of said wire.

8. The device defined in claim 7 wherein said protrusions are disposed in a cylindrical array.

9. The device defined in claim 6 wherein said motion damping element is an elongate axially oriented ridge having a knife-like edge juxtaposed to said wire.

10. A method for removing unwanted material from a vascular system of a patient, comprising the steps of:
    providing a wire surrounded by a sheath;
    threading said wire through labyrinthine vascular passages until a distal end of said wire is disposed at the location of the unwanted material;
    generating an ultrasonic waveform at a proximal end of said wire;
    transmitting said waveform axially along said wire from said proximal end; and
    damping transverse motion of the wire while permitting axial motion of said wire during transmission of said waveform along said wire, said step of damping including the step of touching or holding said wire at a plurality of predetermined points spaced along said wire.

11. The method defined in claim 10 wherein said predetermined points are axial motion nodes.

12. The method defined in claim 11 wherein said step of touching or holding is implemented only at said axial motion nodes.

13. A method for removing unwanted material from a vascular system of a patient, comprising the steps of:
    providing a wire surrounded by a sheath;
    threading said wire through labyrinthine passages until a distal end of said wire is disposed at the location of the unwanted material;
    generating an ultrasonic waveform at a proximal end of said wire;
    transmitting said waveform axially along said wire from said proximal end; and
    damping transverse motion of the wire while permitting axial motion of said wire during transmission of said waveform along said wire, said step of damping including the step of touching or holding said wire along a predetermined length thereof, said predetermined length of said wire moving axially under action of said waveform.

14. An ultrasonic angioplasty device for use with an ultrasonic waveform generator, comprising:
    a wire having a proximal end operatively connectable to said waveform generator and a distal end opposite to said proximal end;
    a ball attached to said wire at said distal end; and
    a sheath surrounding said wire, said sheath having a distal end proximate to the distal end of said wire, said sheath being narrowed at its distal end so that said sheath is in close juxtaposition to said wire around the circumference, proximate to said ball, whereby transverse motion of the wire is minimized while permitting axial motion of said wire during transmission of an ultrasonic waveform along said wire.

15. An ultrasonic angioplasty device for use with an ultrasonic waveform generator, comprising:
    a wire having a proximal end operatively connectable to said waveform generator;
    a sheath surrounding said wire; and
    transverse motion damping means disposed within said sheath for minimizing transverse motion of the wire while permitting axial motion of said wire during transmission of an ultrasonic waveform along said wire, said motion damping means including a plurality of projections extending radially inwardly from said sheath towards said wire, said projections being spaced from one another, thereby permitting a fluid to flow between said wire and said sheath, said projections including a plurality of hair-like protrusions extending inwardly from said sheath, each of said protrusions having a free end in engagement with said wire.

16. The device defined in claim 15 wherein said protrusions are disposed at a predetermined axial motion node along said wire, said protrusions being circumferentially spaced from one another to permit fluid flow between said wire and said sheath and past said node.

17. The device defined in claim 15 wherein the free ends of said hair-like protrusions are in engagement with said wire along a predetermined length of said wire including a predetermined axial motion node and a region of axial motion of said wire.

18. The device defined in claim 17 wherein said protrusions are disposed in a cylindrical array.

19. An ultrasonic angioplasty device for use with an ultrasonic waveform generator, comprising:
   a wire having a proximal end operatively connectable to said waveform generator;
   a sheath surrounding said wire; and
   transverse motion damping means disposed within said sheath for minimizing transverse motion of the wire while permitting axial motion of said wire during transmission of an ultrasonic waveform along said wire, said motion damping means including a plurality of projections extending radially inwardly from said sheath towards said wire, said projections being spaced from one another, thereby permitting a fluid to flow between said wire and said sheath, said projections being located at an extreme distal end of said sheath in part to maintain fluid pressure in said sheath at a predetermined level.

20. An ultrasonic angioplasty device for use with an ultrasonic waveform generator, comprising:
   a waveguide wire having a proximal end operatively connectable to said waveform generator;
   a sheath surrounding said wire; and
   a transverse-motion-damping wire separate from said sheath and said waveguide wire and disposed within said sheath along an area of axial motion of said waveguide wire so as to minimize transverse motion of the waveguide wire while permitting axial motion of said waveguide wire during transmission of an ultrasonic waveform along said waveguide wire.

21. An ultrasonic angioplasty device for use with an ultrasonic waveform generator, comprising:
   a wire having a proximal end operatively connectable to said waveform generator;
   a sheath surrounding said wire; and
   transverse motion damping means disposed within said sheath for minimizing transverse motion of the wire while permitting axial motion of said wire during transmission of an ultrasonic waveform along said wire, said sheath having an indentation in a wall of said sheath, said indentation defining a dimple along an inner surface of said sheath, said motion damping means including said dimple.

22. The device defined in claim 21 wherein said dimple is one of a plurality of dimples located in a transverse plane including an axial motion node of said wire.

23. A method for removing unwanted material from a vascular system of a patient, comprising the steps of:
   providing a wire surrounded by a sheath;
   threading said wire through labyrinthine vascular passages until a distal end of said wire is disposed at the location of the unwanted material;
   generating an ultrasonic waveform at a proximal end of said wire;
   transmitting said waveform axially along said wire from said proximal end; and
   damping transverse motion of the wire while permitting axial motion of said wire during transmission of said waveform along said wire, said step of damping including the step of maintaining, in said sheath and along an area of axial motion of said wire, a solid transverse-motion-damping element separate from said sheath and said wire.

* * * * *